United States Patent [19]

Sterling

[11] Patent Number: 4,481,323

[45] Date of Patent: * Nov. 6, 1984

[54] HYDROCARBON BLOCK COPOLYMER WITH DISPERSED POLYSILOXANE

[75] Inventor: Robert E. Sterling, New Port Richey, Fla.

[73] Assignee: Medical Research Associates, Ltd. #2, Clearwater, Fla.

[*] Notice: The portion of the term of this patent subsequent to May 31, 2000 has been disclaimed.

[21] Appl. No.: 266,093

[22] Filed: May 21, 1981

Related U.S. Application Data

[63] Continuation-in-part of Ser. No. 147,475, May 7, 1980, Pat. No. 4,386,179.

[51] Int. Cl.$^3$ .................. C08L 25/10; C08L 9/06
[52] U.S. Cl. .................... 524/269; 524/572; 524/505; 524/574; 524/575; 525/92; 604/96
[58] Field of Search ............ 525/92; 524/269, 572, 524/574, 575, 505

[56] References Cited

U.S. PATENT DOCUMENTS

| | | | |
|---|---|---|---|
| 3,485,787 | 12/1969 | Haefele et al. | 524/577 |
| 3,578,481 | 5/1971 | Young | 524/269 |
| 4,292,222 | 9/1981 | Grigo et al. | 525/106 |
| 4,386,179 | 5/1983 | Sterling | 524/269 |

*Primary Examiner*—Wilbert J. Briggs, Sr.
*Attorney, Agent, or Firm*—Sherman & Shalloway

[57] ABSTRACT

This invention provides a composition of matter composed of a substantially uniform mixture of a thermoplastic elastomeric hydrocarbon black copolymer and 0.1 to 12 percent by weight of the composition of a polysiloxane. The composition exhibits improved surface, elasticity, and tensile strength characteristics as well as superior processability. The block copolymer may comprise blocks of styrene-ethylene-butylene-styrene in which the styrene blocks have a molecular weight of 5,000 to 40,000 and the ethylene-butylene block has a molecular weight of 20,000 to 500,000. Mineral oil and polypropylene are preferably dispersed in the composition. Combining the copolymer with the polysiloxane typically occurs under the influence of a pressure of 1,500 to 2,500 p.s.i. or above, such as provided by extrusion blending. The resulting elastomeric composition may be extruded into sheets as thin as 0.015, 0.010, or even 0.005 inch, which a puller may thin even further. The resulting composition has a surface smoothness microscopically characteristic of silicone rubber. As one of its many varied uses, the elastomer may find use as an inflatable cuff or balloon on such medical devices as endotracheal tubes. The high elasticity of the composition permits it to act, when in the trachea, as a high residual volume type endotracheal tube, except that it avoids the folds which permit aspiration fluids to channel to the patient's lungs. The pressure it exerts against the tracheal wall falls even below the high volume device. When not inflated, the material returns to a sufficiently small volume that it acts as a low volume device for ease of insertion and withdrawal.

25 Claims, 17 Drawing Figures

PRIOR ART

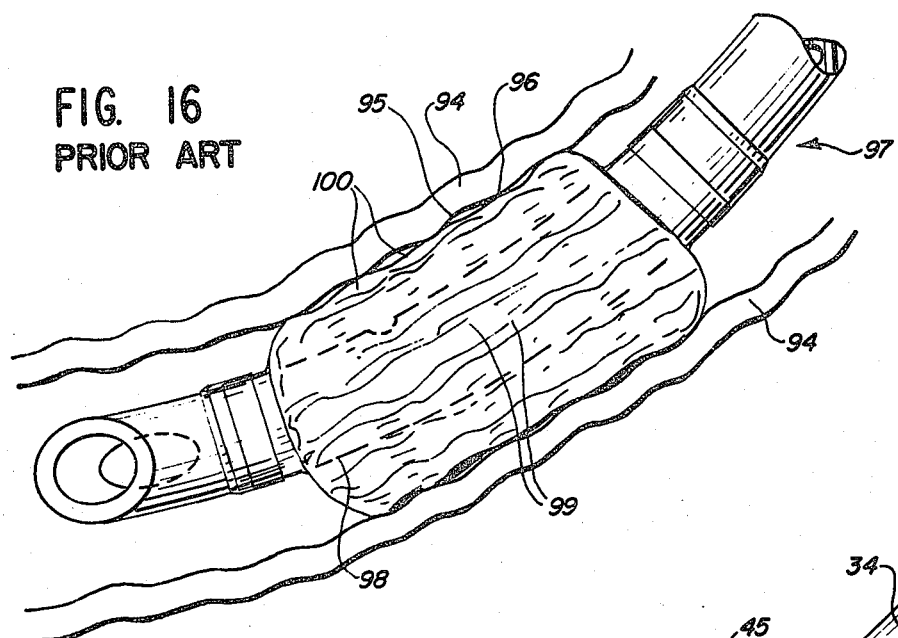
FIG. 16 PRIOR ART
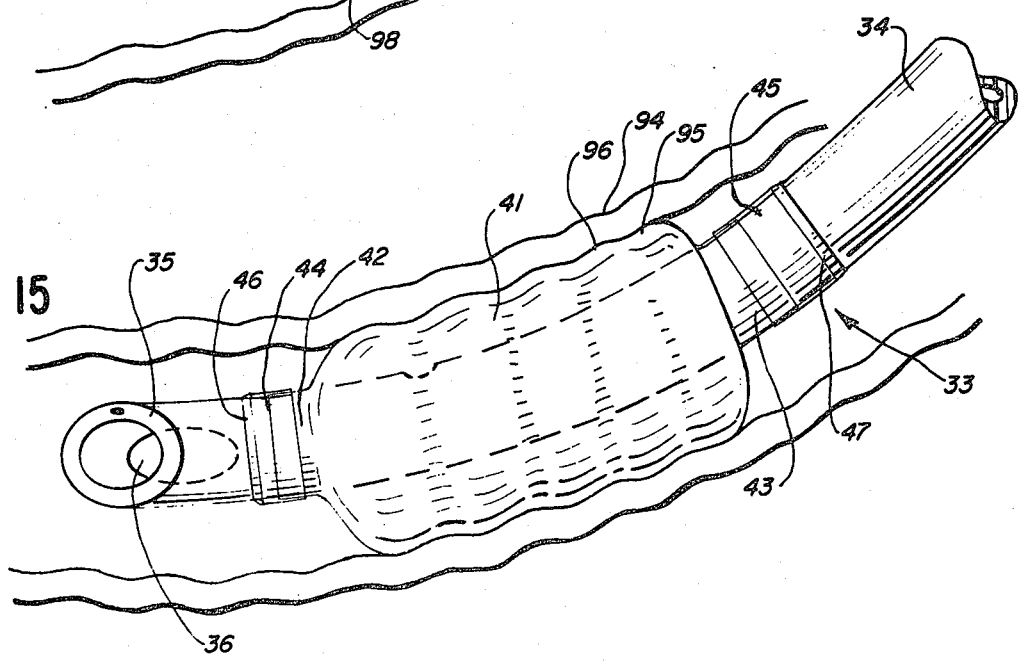
FIG. 15
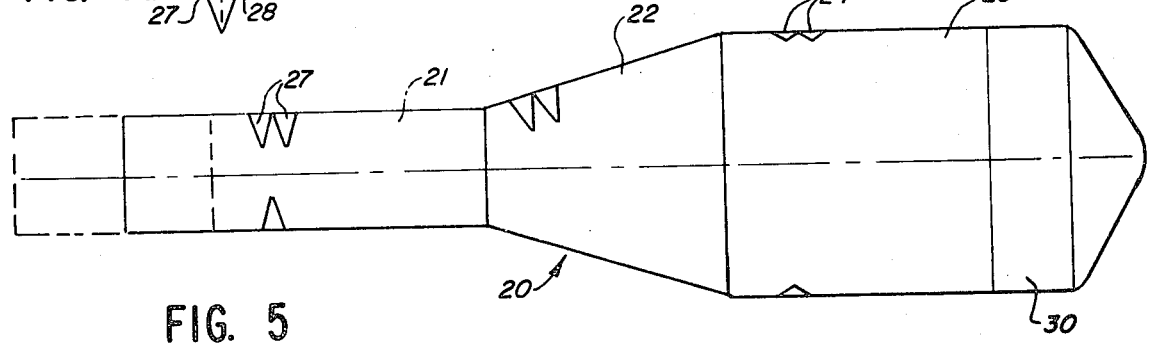
FIG. 5a
FIG. 5

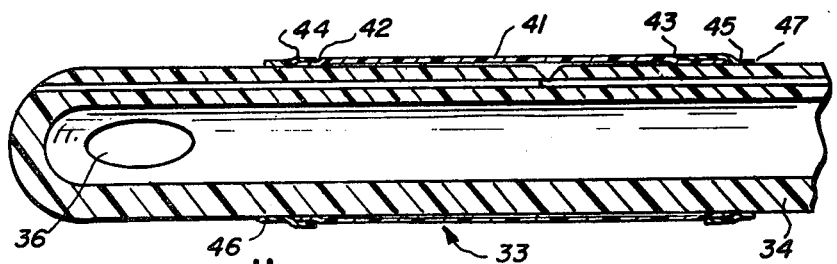
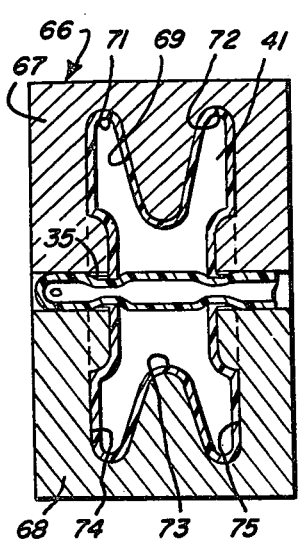
FIG. 9
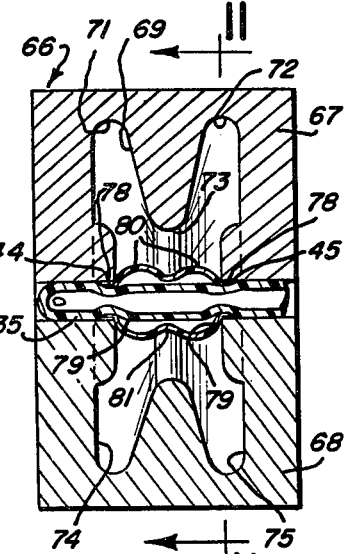
FIG. 10
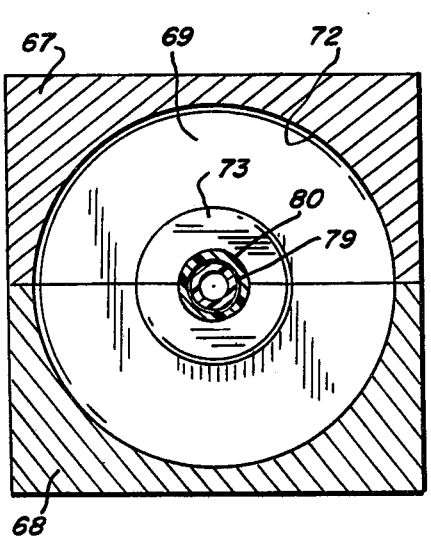
FIG. 11
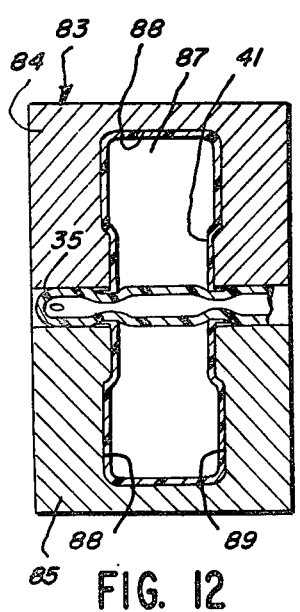
FIG. 12
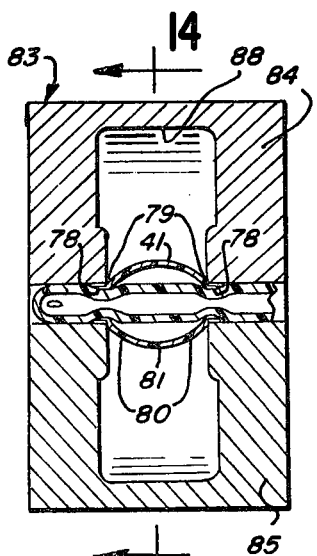
FIG. 13
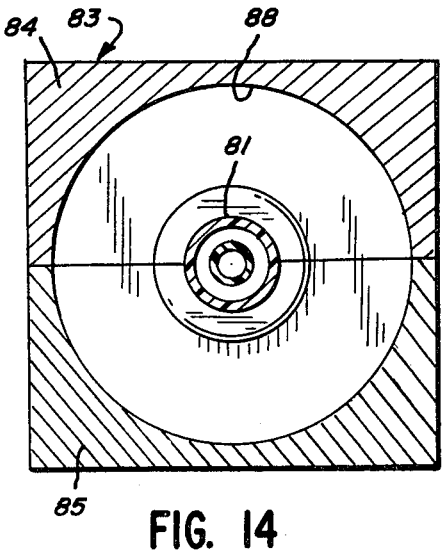
FIG. 14

HYDROCARBON BLOCK COPOLYMER WITH DISPERSED POLYSILOXANE

CROSS REFERENCE TO RELATED APPLICATIONS

This application is a continuation-in-part application of Ser. No. 147,475, filed May 7, 1980 now U.S. Pat. No. 4,386,179.

BACKGROUND OF THE INVENTION

The altered compositions of different polymeric materials provide them with significantly different properties. Modifying a particular molecular composition may allow for the production of a material having specific properties required for a particular use.

Recent work has investigated the possibility of producing a thermoplastic material with elastomeric properties. Elastomers generally take the form of thermoset, as opposed to thermoplastic, polymers. For example, natural and manmade rubbers undergo the necessary step of vulcanization in their production. The resultant cross-linked mass cannot melt under the influence of heat. Rather, it merely burns. Silicone rubbers, having a polysiloxane structure, also undergo cross-linking to produce their elastomeric properties. Again, they do not melt when heated.

In their series of U.S. Pat. Nos. 3,485,787; 3,830,767; 4,006,116; 4,039,629, and 4,041,103, the Shell Oil Company has attempted to provide an elastomer with thermoplastic properties through the use of block copolymer formulations. Typically, a block copolymer has a formula of

A—B—A.    (1)

In the thermoplastic elastomers, the middle block B of the copolymer possesses the desired elastomeric properties.

However, unlike the commonly used rubber materials, the elastomeric middle blocks do not cross-link throughout the material to provide an integral mass. Rather, the terminal blocks A provide the requisite cohesion between the macromolecules. These terminal blocks apparently bond together in the usual thermoplastic fashion. In Shell's material, the terminal thermoplastic blocks represent a minor portion of the macromolecules' total weight. Accordingly, they adhere to each other in the form of relatively small particles embedded within the elastomeric mass of the middle B blocks.

For the terminal blocks A, Shell typically employs polymers formed from monoalkenyl arenes, of which styrene represents a typical example.

For the middle block B, Shell uses a conjugated diene polymer. Butadiene and isoprene provide examples of the elastomeric middle blocks.

The copolymer may contain more than three blocks suggested for formula (1) above. Thus it may have several interspersed A and B blocks linearly interconnected as

A—B—A—B—A—B.    (2)

Alternately or additionally, the block copolymer may have blocks with a branched connection to the main chain as

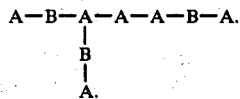

Or, it may have a simple A—B structure. In the ensuing discussion, the simple formula (1) will encompass all of these variations with B representing the elastomeric block. The letter A will designate the thermoplastic binding block which constitutes the terminal blocks on a three-block molecule. The block copolymers may include various other ingredients such as mineral oil, polystyrene, polypropylene and antioxidants.

In their U.S. Pat. No. 3,485,787, assigned to Shell, W. R. Haefele, et al. incorporate mineral oil to extend the block copolymer. In this particular patent, the middle elastomeric block undergoes hydrogenation to produce an ethylene-butylene block from a butadiene block. To prevent bleeding of the extending oil, N. J. Condon, in U.S. Pat. No. 3,830,767, incorportes a petroleum hydrocarbon wax into the block copolymer.

R. J. G. Dominquez, in Shell's U.S. Pat. No. 4,006,116, and G. R. Heimes, et al., in U.S. Pat. No. 4,039,629, create blends of styrene-ethylene-butylene-styrene block copolymers having different molecular weights for both the styrene end blocks and the ethylene-butylene middle blocks. These blends apparently produce a product having superior characteristics for their intended footwear use.

S. Davidson, et al., in their U.S. Pat. No. 4,041,103, blend a styrene-ethylene-butylene-styrene block copolymer with a polyamide polymer. The patent states that the product achieves improved dimensional stability at high temperatures.

Notwithstanding the various efforts to produce a high quality thermoplastic elastomer, the resulting materials do not display many of the qualities associated with the usual rubber materials. For example, when extruded the thermoplastic elastomers do not have the surface smoothness nor the elasticity of the natural, manmade, or silicone rubbers.

A particular need for an improved thermoplastic material, especially with elastomeric properties, appears in the medical field. Notwithstanding the array of available plastics, the problems of toxicity, incompatibility, surface roughness, lack of flexibility, and others have not submitted to a completely satisfactory solution.

D. H. Kaelble, in U.S. Pat. No. 4,123,409, provides a thermoplastic elastomer primarily for sealing a stoma passing through human tissue. The material utilizes a block copolymer having thermoplastic terminal blocks and an elastomeric intermediate block. The copolymer receives an equal amount of high molecular-weight oil compatible and associatable with the elastomeric block of the copolymer. Thus, a copolymer having a hydrocarbon elastomeric block will incorporate a hydrocarbon mineral oil in order to achieve its desired improvement. Similarly, where a polysiloxane represents the elastomeric block, a silicone oil forms part of the end product. The resulting materials, according to the patent display an increased pliancy as well as an ability to wet skin.

R. K. Bernstein et al, in their U.S. Pat. No. 3,034,509, add about 0.15 to 1.00 percent by weight of a silicone oil to polyethylene used in surgical tubing. The addition of the silicone oil reduces the blood's toxic reaction to the tubing. It also helps retard blood coagulation where the tubing contacts living tissue for extensive periods of time.

The endotracheal tube represents a further medical device which also receives a substantial investment of time and effort to improving it. The problems associated with an endotracheal tube receive a discussion in W. Wu, et al., *Critical Care Medicine*, 1, 197(1973), U. Nordin, *Acta Otorlaryngol Suppl.*, 345, 7(1975), and W. N. Bernhard, et al., *Anesthesiology*, 48, 413(1978). These articles focus on the inflatable cuff surrounding the main shaft of the endotracheal tube. The cuff securely lodges the endotracheal tube within the patient's trachea at the location determined by the anesthesiologist. Further, the cuff should completely fill at least a portion of the trachea to prevent aspiration fluids, such as saliva, from passing through the trachea to the patient's lungs.

Two types of cuffs currently find use on endotracheal tubes. The less preferred cuff utilizes a relatively inflexible, or low complaint, material. When deflated, it has a low residual volume. The "low-volume" cuff requires a large internal inflating pressure in order to expand its walls to make contact with the trachea. Any inflation beyond the point of this minimal contact generally results in the exertion of a very large pressure against the tracheal wall. This large lateral wall pressure can so seriously damage the trachea that the patient's death may in fact result.

The second type of endotracheal tube uses a cuff having a highly compliant wall and, when deflated, a large residual volume. One method of forming the high volume cuff involves placing a low volume cuff formed of polyvinylchloride in boiling water. Overinflating the cuff stretches the low volume cuff to form the large cuff.

Excessive inflation of the high volume endotracheal tube in actual use results in the exertion of less lateral wall pressure against the trachea than the low volume type. Nonetheless, the high volume endotracheal tube can still severely damage the patient's trachea. And, since it contacts a larger area of the trachea, its deleterious effects damage more of the trachea than the lower volume models.

Moreover, the deflation of the high volume cuff produces folds in the cuff's wall, a phenomenon referred to as "pruning." When expanding within the trachea, the high volume cuff does not normally expand to its full dimension. If it did, it would then exhibit the same deleterious effects as the low volume cuff. However, expansion to less than its full volume results in the cuff's wall retaining at least some of its folds. These folds, however, provide channels for the aspiration fluids to pass into the patient's lungs. The wrinkles also leave deep grooves in the trachea's mucosal lining.

Generally, the cuffs of the endotracheal tubes have a polyvinylchloride composition which, with its rough surface, can irritate the patient's trachea. Furthermore, the polyvinylchloride includes plasticizers which can leach and induce toxic reactions.

Other cuffs on endotracheal tubes have a latex or a silicone rubber composition. Both of these represent thermoset materials which require dipping and lengthy curing. As a consequence, both have nonuniform surfaces which can also irritate the trachea. Moreover, they can have pinholes and generally display a high rejection of the final product. Moreover, as thermoset plastics, a rejected item cannot undergo salvage and reuse.

Further, each product must undergo thorough testing to assure that it meets the necessary standards. Even with a perfect product, the rubber materials display substantial gas permeability. As a consequence, the internal pressure of the cuff can increase or decrease depending upon the surrounding atmosphere in the trachea. Either event would, of course, produce deleterious consequences. Increasing the pressure further irritate the trachea; decreasing the pressure may allow for the leakage of aspiration fluids around the cuff.

U.S. Pat. No. 4,154,244, to L. F. Becker, et al. suggests using a block copolymer similar to the Shell materials above for both the tube's shank and cuff. Specifically, Becker, et al. utilize different formulations of the styrene-ethylene-butylene-styrene block copolymer to achieve the different properties of the inflatable cuff as opposed to the substantially rigid shank. Moreover, the material has a rough surface which can irritate the patient's trachea. Also, the composition does not extrude into extremely thin sections which would provide the cuff with the desired high degree of pliancy. Accordingly, the search for improved materials for endotracheal tubes continues.

SUMMARY OF THE INVENTION

The present invention provides a composition of matter comprising a substantially uniform mixture of an elastomeric thermoplastic hydrocarbon block copolymer and a polysiloxane. The composition, which may contain more than one hydrocarbon block copolymer, posesses physical and surface properties previously provided only by vulcanized, or cross-linked, rubbers. The present composition with the polysiloxane and the copolymer submits to processing and extrusion to a thinness not previously achieved with hydrocarbon block copolymeric thermoplastic elastomers.

Dispersing the polysiloxane throughout a thermoplastic elastomeric hydrocarbon results in a composition which can display a remarkably smooth surface. Specifically, the surface may have a smoothness comparable on a microscopic scale to that of silicone rubber.

Typically, the composition comprises from 0.1 to 12 percent or more, by weight, of the polysiloxan and more than about 30% by weight of the block copoymer. This represents an unusual result primarily because of the dissimilar nature of the polysiloxane molecule compared to the hydrocarbon backbone of the elastomeric macromolecule.

The polysiloxane content of the composition becomes even more unusual where the latter includes an appreciable amount of mineral oil. In fact, the mineral oil may even represent 60 percent of the composition's total weight. Nonetheless, the composition appears able to take up an appreciable amount of polysiloxane and achieve the beneficial results.

The composition may contain up to 25 percent polystyrene and also include other additives such as polypropylene, generally in an amount less than 45 percent of the total weight of the composition. To render the composition x-ray opaque, barium sulfate may be added. Foaming agents may also allow the composition to take the form of a cellular density product. In addition, antioxidants may be included in the composition.

The block copolymer may have an A—B or preferably A—B—A configuration in which A takes the form of a monovinyl arene polymer block. To provide the elastomeric properties, B may be a hydrogenated or nonhydrogenated conjugated diene polymer block.

The styrene-ethylene-butylene-styrene macromolecule represents a prime example of this type of block copolymer, wherein the styrene blocks typically constitute about 20 to 50 percent of the copolymer's weight while the ethylene-butylene block provides the remaining 50 to 80 percent. The styrene blocks themselves normally have a molecular weight in the range of 5,000 to 40,000. The ethylene-butylene block has a molecular weight greatly exceeding that of the styrene blocks and falling within the approximate range of 20,000 to 500,000. The total molecular weight of the copolymer typically ranges from 50,000 to 600,000.

When more than one block copolymer is used to prepare the present composition, the block copolymers have different contents of terminal A blocks and middle B blocks.

The polysiloxane, which is an essentially linear polysiloxane, has a kinematic viscosity within the range of about 20 to about $10^6$, preferably about 200 to 13,000 centistokes at room temperature (20° to 25° C.). A typical example of the polysiloxane is silicone oil. The polysiloxane has the repeating structure:

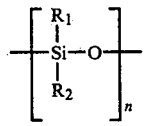

wherein $R_1$, $R_2$ = H, $CH_3$, or

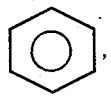

with $CH_3$ being preferred, and n is a positive in having a value ranging from 10 to 20,000.

Preparing the elastomeric composition involves first forming a mixture of the elastomeric thermoplastic hydrocarbon block copolymer with the polysiloxane. This mixture then receives sufficient heat to melt the copolymer. The application of pressure to the melted mixture intimately combines the components to produce the elastomer composition. The steps of heating the mixture and the application of the shearing pressure usually take place in an extruder. Increasing the pressure applied to the melted mixture appears to improve the properties of the final product. The extruder may even have a large portion, for example 40 percent, of the flights on its screw in its metering section and a compression ratio of 4 to 1 or even greater. The pressure thus applied to the melted mixture may well approach 1,500 p.s.i., 2,500 p.s.i., or even much higher.

The elastomeric composition with the polysiloxane may find use in various types of medical devices. The polysiloxane appears to improve the suitability of the elastomer for long term contact with human tissue.

One of the medical devices which can employ the present polysiloxane-containing hydrocarbon elastomer includes a shaft in the form of an elongated hollow tube through which fluid can pass. An inflatable fluid-tight container surrounds the tube between its ends. Located near one of the tube's ends, it anchors the tube at a particular location in the patient's body. Foley catheters and endotracheal tubes represent this type of medical device.

The device must then also have a pressure means to introduce an inflating fluid pressure into the container. It must do so without access to the end near which the container sits. Generally, the container and the end closest to it are located inside the patient's body which, of course, prohibits any access thereto. Usually, this pressure device takes the form of a canal running inside of the wall of the main shaft of the device. The container, or cuff, may advantageously have a composition of a thermoplastic elastomeric hydrocarbon block copolymer having an essentially linear polysiloxane distributed substantially uniformly throughout.

The block copolymer with the polysiloxane appears extremely inert to human tissue. Thus, the inflatable container of an endotracheal tube can remain contact with the tracheal wall without irritation due to toxic reactions.

Furthermore, the greater elastic compliancy in thin sections possessed by the present material allows for its inflation past the pressure where it seals against the trachea. By minimizing the lateral wall pressure, this material avoids many of the complications induced by other endotracheal tubes currently in use.

The great elasticity of the present polysiloxane-containing copolymer along with its low residual volume allows it to expand uniformly against the tracheal wall to provide a complete seal. Thus is prevents the aspiration of fluids into the patient's lungs.

Moreover, its elasticity also permits the container wall, upon deflation, to contract tightly against the tube's shaft without developing folds. In addition, the material has an extremely smooth surface. Together, these features help avoid damage to the tracheal wall upon the insertion, retention, and removal of the device.

Where the device's shaft and the inflatable cuff have compatible compositions which wet each other, a heat seal may suffice to adhere them together. However, the two compositions may lack such compatibility. This represents the situation when using a shaft of polyvinylchloride. In this instance, heat shrinkable plastic sleeves may adhere the silicone-containing polymer to the shaft. Part of the shrinkable sleeves, after going through the heat shrinking process, should then contact the shaft itself. A bead of cement then assures a tight seal between the sleeves and the tube's main shaft.

The improved processing qualities imparted by the polysiloxane to the elastomeric, thermoplastic hydrocarbon block copolymer permit the extrusion of the composition into extremely thin sheets. In fact, the composition may extrude in the form of a web through an orifice having a thickness no greater than about 0.015 inch. In fact, it can extrude properly through an orifice as small as 0.005 inch or less.

Furthermore, the material may have its thickness reduced even further if it is subjected to pulling after extrusion. When extruded in the form of a tube, the material can withstand an internal air pressure as an aid in retaining the tube's shape.

BRIEF DESCRIPTION OF THE FIGURES

FIG. 5 depicts an extruder screw modified to apply a large shearing pressure to a molten thermoplastic polymer.

FIG. 8 depicts an endotracheal tube with a cuff formed of an elastomeric thermoplastic copolymer with dispersed polysiloxane prior to the cuff's shaping.

FIG. 9 is the cuff of an endotracheal tube undergoing the first step of an orientation process in a clover-leaf-shaped mold.

FIG. 10 shows the endotracheal tube of FIG. 8 after it has undergone the shaping process depicted in FIG. 9.

FIG. 11 gives a cross-sectional view along the line 11—11 of the mold and preliminarily shaped endotracheal tube of FIG. 10.

FIG. 12 shows an endotracheal tube undergoing a second shaping step in a rectangularly-shaped mold.

FIG. 13 shows an endotracheal tube that has undergone both the shaping in the cloverleaf-shaped mold in FIGS. 9 through 11 and the second shaping step of the mold in FIG. 12.

FIG. 14 gives a cross-sectional view along the line 14—14 of the mold and endotracheal tube with shaped cuff shown in FIG. 13.

FIG. 15 shows a partially broken away view of an endotracheal tube in a patient's trachea where the tube's cuff has a composition of an elastomeric, thermoplastic hydrocarbon block copolymer with dispersed polysiloxane.

FIG. 16 depicts an endotracheal tube of the prior art placed in the patient's trachea and where the tube's cuff has a composition of polyvinylchloride.

DETAILED DESCRIPTION OF THE INVENTION

According to the present invention, adding a polysiloxane, preferably silicone oil, to one or more elastomeric, thermoplastic hydrocarbon block copolymers accomplishes several distinct and desirable results. Initially, the material displays a substantial improvement in its processibility. This has particular importance when the material is extruded into thin webs. Without the polysiloxane, the material appears to have flow and surface properties which cause the molten plastic to form globules, thus a rough surface, upon departing the extruder's orifice.

The tendency of the molten material to agglomerate interferes with its processing in several ways. Initially, the extruded material cannot achieve a high degree of surface smoothness. As the molten material attempts to form globules, the surface becomes characterized with hills, valleys, and even craters. The polysiloxane, by apparently decreasing the surface energy of the molten material, allows the extruded plastic to solidify with a very smooth surface.

Figure 1:
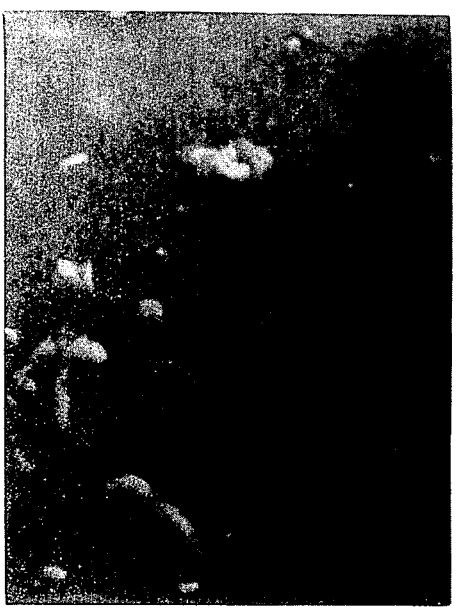
FIG. 1 provides an electron photomicrograph with an enlargement of 2,000× of the surface of an elastomeric, thermoplastic, hydrocarbon block copolymer incorporating 3 percent by weight of dispersed polysiloxane.

FIG. 1 shows an electron photomicrograph of the surface of a thermoplastic elastomeric hydrocarbon block copolymer with dispersed polysiloxane. The photomicrograph, with an enlargement of 2,000×, shows dust particles on the elastomer's surface. The material shown in FIG. 1 has a composition of an A—B—A block copolymer with polystyrene representing the end blocks and ethylene-butylene copolymer as the middle block. It also includes about 50 percent by weight mineral oil, 5 percent polypropylene, possibly polystyrene and various antioxidants. The Shell Chemical Company of Houston, Tex., sells the basic polymer without the polysiloxane under the designation of Kraton G 2705. The polysiloxane, constituting about 3 percent by weight of the final composition, is dispersed within the block copolymer according to the process described below. The Dow Corning Company of Midland, Mich., provides the polysiloxane as 360 Medical Grade devolatilized silicone oil. Suitable antioxidants include Irganox, a product of Ciba-Geigy Corporation.

Figure 2:
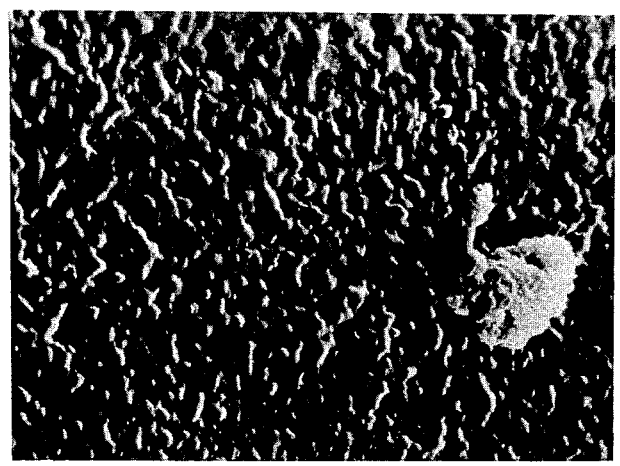
FIG. 2 displays an electron photomicrograph, also at 2,000×, of the surface of a plasticized polyvinylchloride frequently used to form the cuffs of endotracheal tubes.
Figure 3:
FIG. 3 shows the surface, under 2,000× magnification, of a latex rubber material.
Figure 4:
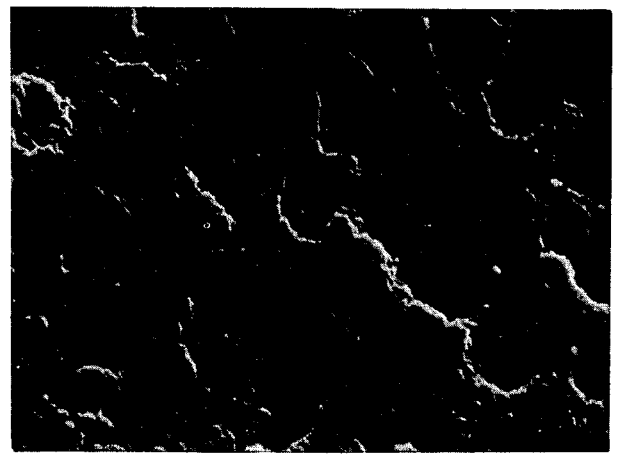
FIG. 4 shows an electron photomicrograph at 2,000× of the surface of silicone rubber.

Comparable photomicrographs showing other materials in common use for medical purposes, especially the cuffs of endotracheal tubes, appear in FIGS. 2 to 4. Each of these has the same magnification as FIG. 1.

Specifically, FIG. 2 shows the surface of an endotracheal tube cuff made of plasticized polyvinylchloride. This composition has found wide use in endotracheal tubes. The photomicrograph readily reveals substantial surface irregularities. This surface roughness irritates and damages the patient's mucosal lining.

FIG. 3 shows the surface, also under 2,000× magnification, of a latex rubber material. Again, the readily apparent surface roughness has an irritating effect upon the patient.

FIG. 4 provides a view of the surface of an endotracheal tube cuff formed of a silicone rubber. The photograph reveals some tendency of the rubber to form globules. Aside from that, the surface appears relatively smooth. A comparison of FIGS. 1 and 4 shows that the thermoplastic hydrocarbon block copolymer with the dispersed polysiloxane has a surface smoothness comparable to or even exceeding that of the silicone rubber.

The surface effects produced by the polysiloxane appear to derive from a slightly increased concentration of silicone molecules at the composition's surface. The processing techniques discussed below should typically result in a uniform dispersement of the polysiloxane throughout the composition. However, a slight migration of the silicone molecules to the material's surface occurs. As a result, the material's surface, to a depth of about 5.0 to 20.0 nm., appears to have a concentration of silicone molecules approximately twice that of the bulk of the material. The thinness of this layer, of course, prevents the greater concentration there from affecting the bulk concentration of the polysiloxane throughout the material. Consequently, on a macroscopic scale, the material has a substantially uniform dispersement of the polysiloxane. This gives the surface substantially different properties than the hydrocarbon block copolymer without the polysiloxane.

Both the surface smoothness and concentration of polysiloxane portend a blood compatibility of the material. Both factors reduce the likelihood of the attachment and clotting of blood components to the polymer.

The Shell patents listed in the "Background" section above give a general discussion on elastomeric thermoplastic hydrocarbon block copolymers. The information given in those references, as well as Shell's U.S.

Pat. No. Re. 27,145 of R. C. Jones, has general applicability to the discussion of thermoplastic rubbers below.

Typically, the middle or B, block of the A—B—A elastomeric hydrocarbon block copolymer provides the molecule with its elastomeric properties; the B blocks themselves possess the rubber qualitites. Polymers formed from conjugated dienes have found favor in this role. Butadiene and isoprene represent monomers which, after polymerization, have provided the middle, elastomeric block. Furthermore, the butadiene block may undergo hydrogenation to become an ethylene-butylene copolymer elastomeric block.

The resulting block copolymer typically has its mechanical properties determined primarily by the elastomeric B block. Accordingly, the middle block should provide at least a majority of the block copolymer's total molecular weight. In fact, it usually provides 50 to 80 percent of the molecular weight of the final product. The molecular weight of the middle B block usually falls within the range of 20,000 to 500,000 and typically comes within the narrower range of 20,000 to 200,000.

The terminal, or A, blocks of the copolymer provide the cohesiveness between the individual macromolecules in the thermoplastic rubber. These terminal blocks themselves behave as a thermoplastic. They do not usually display any elastomeric quality. However, representing a minority of the weight of the final elastomer, they do not impart their own mechanical properties to the product.

The thermoplastic adherence between molecules of the A blocks replaces the vulcanization of the natural, latex, or silicone rubbers. In vulcanization, actual chemical bonds develop between the macromolecules constituting the rubber. These crosslinking reactions generally occur at elevated temperatures and thus impart the name "thermoset" to the materials. These rubbers generally require extensive periods of time to "cure" or undergo the required crosslinking. The crosslinking does not represent a reversable process. As a consequence, the nonthermoplastic rubbers, once cured to a particular form, cannot melt to adapt a different form. At elevated temperatures they only oxidize or, in more extreme cases, burn.

The terminal A blocks of the block copolymer adhere to each other through physical attraction bonds characteristic of all thermoplastics. Thus, when in the solid form, the terminal blocks of several molecules adhere to each other to provide the required cohesiveness throughout the material. The adhered terminal blocks form small groups, or "particles," embedded within the predominant elastomeric portions of the material. These particles serve to bind the sundry macromolecules in the mass into an integral whole.

At elevated temperatures, these "particles" of physically bonded terminal blocks of different macromolecules actually melt. The entire mass of material then assumes the liquid or molten state and can undergo the usual processing techniques such as extrusion, blow molding, or injection molding. When cooled, the terminal blocks of different macromolecules again physically bond to each other and form particles. The material then generally retains the shape it possessed when the particles formed by the terminal A blocks coalesced into the solid state.

The class of molecules labelled monovinylarenes have provided suitable thermoplastic terminal A blocks for these polymers. Examples of the monomers which can polymerize into the terminal blocks include isoprene and alphamethyl isoprene. The former of these two has generally received greater use.

The terminal A blocks generally have a molecular weight within the range of 5,000 to 40,000, and most fall within the range of 8,000 to 20,000. The terminal blocks constitute about 20 to 50 percent of the total weight of the macromolecule.

As discussed above, the elastomeric block copolymer molecule may include more than two or three blocks suggested by the A—B—A formula. The macromolecule may contain additional blocks arranged in either the linear or branched fashion suggested by formula (2) and (3). In this eventuality, the thermopoastic A block may not actually represent the terminal blocks at all ends of the molecule. In any event, the macromolecule generally has a total molecular weight falling within the range of 50,000 to 600,000.

As mentioned previously, one or more of the block copolymers may be used in forming the composition. When more than one block copolymer is used, the block copolymers differ from each other with respect to the amounts of terminal A blocks and middle B blocks present therein. For instance, a mixture of a first block copolymer containing about 28 percent by weight styrene block A (e.g., Shell Kraton G 1650) and a second block copolymer containing about 33 percent by weight styrene block A (e.g., Shell Kraton G 1651) can be used. The weight ratio of the first: second block copolymer can vary from 15:85 to 50:50.

The polysiloxane has the following repeating structure:

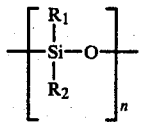

where $R_1$, $R_2$ = H, $CH_3$, or

and n is a positive integer between 10 and 20,000. The readily available silicone oils generally employ the methyl group for both of the radicals $R_1$ and $R_2$. The polysiloxane is essentially linear as shown in the above formula. A preferred example of the polysiloxane is silicone oil.

The viscosity of the polysiloxane should permit its facile coating of and mixing with the crumbs or pellets of the elastomer. This results in a general requirement that the kinematic viscosity within the range of about 20 to 1,000,000 centistokes. At the lower end of the above range, the polysiloxane encounters some difficulty in coating the polymer pellets. As a preferred embodiment, silicone oil having a kinematic viscosity of 200 to 13,000 centistokes works well without complication.

Where the final product has a medical use, a medical grade polysiloxane should be employed. Furthermore, devolatilizing the polysiloxane prior to its introduction to the block copolymer removes very low molecular weight elements that could leach and irritate the patient's tissues.

The polysiloxane generally constitutes about 0.1 to 12 percent of the total weight of the elastomeric composition, preferably from 1 to 7 percent. The ability of the hydrocarbon to take up this amount of the polysiloxane is surprising; the hydrocarbon backbone of the polymer has a drastically disparate nature as compared to the silicone structure of the polysiloxane.

The surprise becomes even greater for polymeric compositions that already include substantial amounts of mineral oil as a lubricant. Mineral oil, if present, may account for up to 60 percent of the total weight of the composition. Typically, the mineral oil constitutes from 25 to 50 percent of the composition's total weight.

Furthermore, the mineral oil and the polysiloxane also have distinctly different chemical properties. The former has a hydrocarbon composition as compared to the silicone of the polysiloxane. Moreover, the mineral oil fills the spaces that would presumably accomodate the polysiloxane. Yet, a composition having 50 percent of mineral oil can still assimilate several percent of the polysiloxane to produce a drastically different elastomer.

Adding polypropylene as a binder to the present elastomeric composition produces a stiffening effect upon the elastomeric composition. The polypropylene also reduces its elasticity slightly. The amount of added polypropylene generally remains less than 45 percent of the composition's total weight. It more usually falls within the range of 2 to 20 percent or in the narrower range of 5 to 10 percent.

The addition of $BaSO_4$ also stiffens the polymeric composition. The $BaSO_4$, of course, also provides the polymeric composition with an opacity to X-rays. Titanium dioxide pigment can also affect the polymer's visual appearance. Polystyrene can help the polymer's rheological properties.

Adding a foaming agent to the polymer during its formulation will give a drastically different type of product. Rather than a substantially solid material, a cellular product filled with air and a drastically reduced density will result. This cellular thermoplastic elastomer will have the general feel of a sponge. Employing a nontoxic foaming agent will allow the medical use of the resulting product. One such nontoxic foaming agent is azobisformamide. Added in the amount of about two percent, it creates $CO_2$ gas. The bubbles of gas, covered by the molten elastomer, produce, after solidification, the sponge-like material. This foamed product may find use as a padding material for wounds.

Preparing the elastomeric composition with the dispersed polysiloxane begins with the hydrocarbon block copolymer. The techniques for preparing the elastomeric thermoplastics appear in many references including the patents referenced above. The inclusion of the usual additives also appears in these discussions.

Mixing the crumbs or pellets of the elastomeric resin, which may be one or more block copolymers having different amounts of the constituent blocks, with the polysiloxane should result in a coating of the former with the latter. To do so, the pellets or crumbs and the polysiloxane may be mixed in a tumbler. Any additional ingredients, such as polypropylene, polystyrene, and/or $BaSO_4$, may also be added to the mixture at this point.

The coated elastomer pellets or crumbs next receive sufficient heat to induce their melting. Applying a shearing pressure to the melted coated crumbs or pellets appears to induce a substantially uniform dispersement of the polysiloxane in the mixture. The heat required to effectuate the melting, of course, depends upon the individual elastomer. Typically, it ranges from 160° C. to 225° C.

After melting the block copolymer by heating, the mixture comprising the block copolymer, the polysiloxane and other suitable ingredients described above may be optionally fed through a plurality of calender rolls to form sheets of the mixture. Thereafter, the sheets are subjected to shearing pressure by feeding the cut strips of sheets to an extruder or a compression molding machine for better dispersement of the polysiloxane.

To ensure adequate dispersement of the polysiloxane, the composition is subjected to an appropriate amount of pressure, usually about 1,500 p.s.i. However, it has been found that by increasing the pressure, further improved properties of the product are obtained. Thus, the molten mixture may be subjected to pressures of 2,500 p.s.i., 3,000 p.s.i., or higher.

An extruder provides the most convenient means of achieving the temperatures and pressures required to disperse the polysiloxane within the composition. An extruder typically has several temperature zones and thus can pass the crumbs or pellets of the polymer through the temperature stages required for melting.

However, the standard extruder may lack the ability to apply sufficient pressure to assure the complete dispersement of the polysiloxane. FIG. 5 shows an extruder screw generally at 20 modified to apply a greater shearing pressure to the resin material.

The screw 20 has the three zones characteristic of most extruder screws. The first section 21, known as the feed zone, initiates the melting of the polymer pellets and moves them along to the compression or transition zone 22. There the polymer generally completely melts and undergoes a sufficient shearing stress to mix the ingredients together. The metering section 23 usually provides the melted resin to the die at a known rate and pressure.

The screw shown in FIG. 5 has a length-to-diameter ("L/D") ratio of 24:1. In this type of screw, the metering section 23 typically has about 20 to 25 percent of the total flights, or pitch lengths, of the entire screw. On the modified screw 20 shown in FIG. 5, the metering section 23 has ten flights 24 of the screw's total of 24.62 flights; the feed section 21 has 6.62 flights 27, and the transition section 22 has eight flights. Thus, for the screw 20, the metering section 23 has 40 percent of the total flights. This large fraction of the flights increases the length of time that the resin remains in the metering section 23 and the amount of pressure applied to it.

Furthermore, as shown in FIG. 5a, the flights 24 of the metering section 23 have a much smaller cross-sectional area than the flights 27 of the feed section 21. In fact, the depth 28 of the feed-section flight 27 amounts to four times the depth 29 of the metering-section flight 24. This high compression ratio of 4:1 drastically increases the pressure applied to the material in the metering section 23. To increase the pressure even further, the compression ratio of the feed-section flights 21 to those in the metering section 23 may even go to 5:1 or higher. As this ratio increases, the material becomes squeezed into the smaller flights 24 and, thus, experiences a greater shearing pressure.

Naturally, the pressure experienced by the polymer in the flights 24 also depends upon the size of the orifice through which it passes when departing the extruder. At the smaller orifice sizes of 0.015, 0.010, or even 0.005 inch, only a small amount of resin leaves the extruder over a period of time. The remainder backs up against the orifice opening and maintains the pressure upon the polymer in the pump section 23.

Larger orifices, of course, allow the pressure in the metering section 23 to dissipate. However, placing a screen, called a breaker plate, adjacent to the screw's torpedo section 30 can retain a sufficient back pressure on the metering section 23. This screen can have a mesh of 100 or finer.

Placing additional obstacles in the path of the molten polymer beyond the breaker plate can also increase the pressure experienced in the metering section 23. Furthermore, a longer land, which is the distance along which the bore of the extruder narrows down to the orifice size, can also retain the desired pressure in the flights 24. A pressure blender and a mixing head can also give increased pressure. An extruder with the appropriate modification can deliver the resin to its die under a pressure of 3,000 p.s.i. at the breaker plate.

Extruders produced by two separate manufacturers have adequately mixed the polysiloxane with the block copolymer. The first, a Brabender extruder, employs a $\frac{3}{4}$ inch, 5:1 compression ratio screw operating at 20 to 105 r.p.m. Its three zones remain at 180° C. while the die is at 170° C. It produces a two-inch sheet of polymer with a width of 0.020 inch.

An HPM extruder (of the HPM Corporation of Mt. Gilead, Ohio) utilizes a $2\frac{1}{2}$ inch screw with a 4:1 compression ratio. The screw operates at 10 to 50 r.p.m. and its zones maintain temperatures of 188° C. to 193° C. The die temperature remains at 200° C.

Once produced, the material, as a thermoplastic, will submit to the usual product-forming techniques. Thus, it can undergo further extrusion to a particular shape, if not achieved in the original extrusion. It can also undergo the usual blow-molding techniques. Moreover, its thermoplastic nature allows the reuse of scraps of material and of rejected parts.

The elastomer with the dispersed polysiloxane can have a wide variety of uses. In fact, the only limitation seems to be the ability to conceive of such uses. It can include the mundane, such as food packaging materials or automobile seat covers. In fact, the thermoplastic elastomer with dispersed polysiloxane retains its elastomeric properties at very low temperatures. Thus, it would appear highly suitable for such uses as the suggested food packaging and seat covers.

Moreover, the thermoplastic elastomer with the dispersed polysiloxane can also have sophisticated uses such as medical appliances. Toxicological tests show that materials produced according to the examples given above remain nontoxic when in contact with human tissue. Furthermore, no negative effects from leaching occurred during a period of seven days of testing. Thus, they can also find use as objects implantable in the human body.

Figure 6:
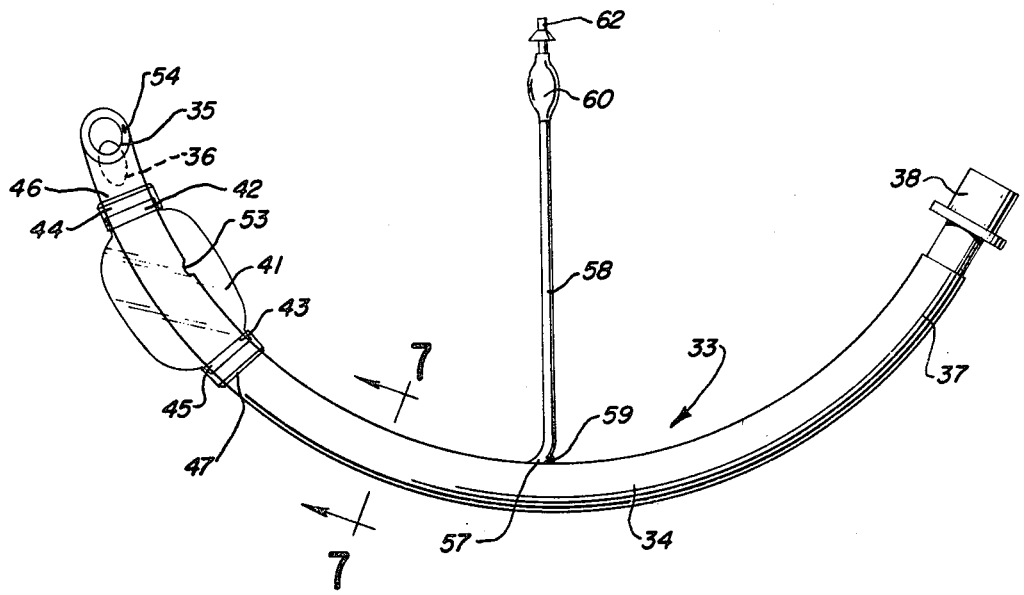
FIG. 6 gives an endotracheal tube having an inflatable cuff formed from an elastoeric, thermoplastic hydrocarbon block copolymer with 4 percent by weight dispersed polysiloxane.

In particular, medical devices having an inflatable balloon on a central shaft can take advantage of the present thermoplastic elastomer composition having polysiloxane dispersed therein. The endotracheal tube, appearing generally at 33 in FIG. 6, provides one example of this type of medical appliance.

The endotracheal tube 33 includes the main shaft 34. The shaft 34 in most endotracheal tubes has a composition of a clear, flexible, medical-surgical grade polyvinylchloride. As stated above, an SEBS thermoplastic elastomer may also find use as the shaft 34. The shaft 34 generally has a substantially rigid construction and a permanent, uniform arc generally with a 130 to 140 mm. radius to facilitate its insertion into the trachea.

The shaft 34 may have an inside diameter ranging from 2.5 mm. to 10 mm. Its length ranges from 240 mm. to 360 mm. depending upon its internal diameter.

The "distal" end 35 has a 30° to 45° angle and a Murphy tip with the eye 36. The end 35 and the eye 36 provide passageways to both of the patient's bronchi if the attendant inserts the tube 33 that far into the trachea.

The other, or "proximal," end 37 of the shaft 34 receives the adaptor 38. It generally has a composition of polypropylene and several companies sell them separately. The adaptor 38 connects to the actual equipment that assists the patient's respiration.

The shaft 34 also carries the inflatable cuff 41. The cuff 41 is formed of the present SEBS block copolymer with the dispersed polysiloxane generally described above. The preferred SEBS block copolymer is Shell Kraton G 2705, which comprises a mixture of styrene and ethylene-butylene in a weight ratio of 28:72. Additionally, the mixture contains 5 percent polypropylene and 45 percent mineral oil by weight. To make the cuff, a composition comprising 4 percent by weight of the polysiloxane and the remainder Shell Kraton G 2705 is formed and processed. The tubing for the cuff 41 typically has a thickness of 0.008 to 0.010 inch.

Having an air-tight compartment with this tubing requires the sealing of the ends 42 and 43 of the cuff 41 to the shaft 34. If the shaft 34 has the same composition as the cuff 41, they can adhere to each other through a heat weld. For example, the ends 42 and 43 and the adjacent portions of the shaft 34 can be melted by sonic welding. The molten material from the components can then comingle, and, after cooling, adhere to each other. In general, the heat sealing of the cuff 41 to the shaft 34 can occur when the materials of these two components are compatible; when melted, they wet each other.

However, in the event that the shaft 34 is formed of polyvinylchloride which lacks compatibility with the SEBS block copolymer of the cuff 41, they cannot be heat sealed. Accordingly, to seal the cuff 41, the shrink sleeves 44 and 45 compress the cuff's ends 42 and 43 against the shaft 34. The shrink sleeves 44 and 45 represent short lengths of clear polyvinylchloride shrinkable tubing. The Gilbreth Internanational Corporation sells this material in a medical-surgical grade as "Skin Tight 430RK." The material, when heated to 300° F. for 3 seconds, forms an air-tight sealing collar around the ends 42 and 43 of the cuff 41 against the shaft 34.

Normally, the shrink sleeves 44 and 45 are sufficient to retain the cuff 41 in position and provide an air-tight seal around the ends 42 and 43 of the cuff. However, the seal may be further maintained by the beads of cement 46 and 47. As a typical example, the cement includes one part by weight of clear 85 duro Food and Drug Administration (FDA) surgical grade polyvinylchloride (PVC) dissolved in five parts of tetrahydrofuran. This mixture then receives seven parts of methyl isobutyl ketone to prepare the final cement. This PVC-based cement will adhere to the polyvinylchloride of both the shaft 34 and the shrink sleeves 44 and 45. After the sleeves 44 and 45 have shrunk to provide an air-tight seal of the cuff 41, the beads of cement 46 and 47 are placed at the junctures of the sleeves 44 and 45 at the shaft 34.

Figure 7:
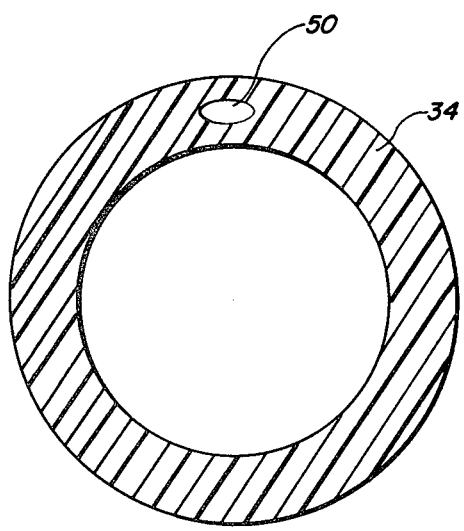
FIG. 7 gives a cross-sectional view along the line 7—7 of the shaft of the endotracheal tube of FIG. 6.

Once placed inside the patient's trachea, the cuff 41 must receive an inflating fluid, usually air, in order to lodge it against the patient's tracheal wall. However, the distal end 35 of the shaft 34 as well as the cuff 41, both inside the patient's trachea, have become inaccessible to direct manipulation by the attendant. Accordingly, the shaft 34, shown in FIG. 7, has the lumen 50 running its entire length. The lumen 50 permits the introduction of the inflating fluid into the cuff 41.

To permit fluid in the lumen 50 to enter the cuff 41, the shaft 34 has the notch 53 cut into it. The notch 53 has a location on the shaft 34 and a sufficient depth to intersect the lumen 50. Accordingly, fluid within the lumen 50 can enter and inflate the cuff 41.

The rod 54 fills the lumen 50 between the notch 53 and the shaft's end 35. This prevents fluid in the lumen 50 from escaping through the lumen's opening in the shaft's end 35. The rod 54, in particular, has a composition of nontoxic PVC with a 70 duro hardness. It may also include 30 percent by weight $BaSO_4$ to make it X-ray opaque. This permits the observation of the insertion of the endotracheal tube 33 into the trachea with the aid of an X-ray machine. A small amount of methyl isobutyl ketone facilitates the insertion and seals the rod 54 in the lumen 50.

The shaft 34 includes a second notch 57 which communicates with the lumen 50. The air inflation tube 58 then enters the lumen 50 through the notch 57. The application of a small amount of the methyl isobutyl ketone solvent should precede the introduction of the tube 58. This allows the tube 58, made of PVC, to adhere to the interior surface of the lumen 50 and provides a fluid-tight seal. A small drop 59 of the same PVC cement described above firmly adheres the tube 58 to the shaft 34.

The inflation tube 58 connects in turn to the pilot balloon 60 formed of dipped plastisol medical-grade PVC. The balloon, having a highly flexible construction, permits the visible monitoring of the inflation pressure actually entering the cuff 41; as the pressure in the cuff 41 increases, so does the size of the pilot balloon 60.

Finally, the pilot balloon connects to the Roberts' valve 62 obtainable from the Halkey-Roberts Corporation. Designated as Roberts' valve A10-ACS, it has a vinyl copolymer composition.

The valve 62 accepts a leur-loc syringe. The insertion of the syringe into the valve 62 permits a change in the fluid pressure inside the cuff 41. Specifically, fluid introduced into the valve 62 passes through the pilot balloon 60, the inflation tube 58, the lumen 50, and the notch 53 to inflate the cuff 41. Similarly, a negative pressure created by the syringe attached to the valve 62 aspirates fluid from the cuff 41 through the notch 53, the lumen 50, the inflation tube 58 and pilot balloon 60.

The cuff 41, after the initial assembly of the endotracheal tube 33, may undergo a forming process prior to its actual use in the patient. Otherwise, the cuff 41 will merely inflate over a very small area intermediate its ends 42 and 43. The forming process results in the cuff 41 inflating over its entire length between the sleeves 44 and 45.

FIG. 8 shows the cuff 41 of the endotracheal tube 33 prior to the final forming and orienting steps. As shown, the thermoplastic elastomeric tube forming the cuff 41 has a diameter of 0.4 inch, a thickness of 0.008 to 0.010 inch, and a length of 2 inches. The PVC sleeves 44 and 45 each have a length of 0.37 inch and half of each of them contacts the shaft 34 while the other half contacts the cuff 41.

To begin the forming process, the end 35 of the endotracheal tube having the cuff 41 enters the mold shown generally at 66. The mold has two halves 67 and 68 formed of time and heat cured R.T.V. molded silicone. The interior surface 69 of the mold 66 has a cross-sectional configuration generally resembling a cloverleaf. The plane showing the cross-sectional views of FIGS. 9 and 10 passes through the center of the mold, and, thus, the center of the endotracheal tube 33.

The wide discs 71 and 72 of the mold 66 each has a diameter of 4.75 inches. The narrow throat 73 of the mold has a diameter of 2 inches. Furthermore, the end surfaces 74 and 75 have a separation of 2 inches from each other.

With the endotracheal tube inside the mold 68, the fluid enters and inflates the cuff 41 until it contacts the mold's interior surface 69. The inflation occurs with the mold 66 maintained at room temperature.

During the inflation in FIG. 9, the portions of the cuff in the region 71 and 72 of the mold expand from a diameter of 0.4 inch to a diameter of 4.75 inches. This almost 12-fold expansion of the cuff 41 causes the material to exceed its elastic limits. As a result, it retains a new orientation and shape, when deflated, from the shape shown in FIG. 9.

The exact inflation required to achieve a permanent orientation depends upon the particular elastomer employed. Less elastic material may require an expansion to only 3 times its original size. For other materials, an expansion to 5 to 8 times the original dimension may suffice.

As shown above, the present composition with the dispersed polysiloxane can undergo an expansion of about 12 times its original size without breaking. Very few other materials, if any, whether thermoplastic or thermoset, can achieve this expansion without substantial and irreparable damage.

Not only does the shape of the cuff 41 undergo alteration during the inflation, so does the thickness of the thermoplastic elastomer forming the cuff. The edges 78 of the cuff 41 remain under the shrink seals 44 and 45 and do not experience any stretching at all. Consequently, they retain their original thickness of 0.008 inch. The cuff portion 79 immediately adjacent the beginning of the mold 66 undergoes a slight expansion and achieves a thinness, after the first expansion step, of 0.007 inch. The regions 80 of the cuff 41 expand into the legs 71 and 72 of the cloverleaf mold 66 and experience the greatest expansion. As a result, they finish the first inflation step with a thickness of 0.005 inch. The middle 81 of the cuff 41 only expands until it contacts the neck 73 of the mold 66. Its thickness reduces to 0.006 inch.

If the endotracheal tube underwent use with the cuff 41 having the configuration shown in FIGS. 10 and 11, it would not inflate along its entire length against the patient's trachea. The cuff 41 would experience two principal areas of inflation around the bulges 80 shown in FIG. 10. This would provide two small areas of contact against the patient's trachea, with the middle portion 81 not expanded to make contact. Accordingly, the cuff 41 undergoes the shaping step illustrated in FIG. 12.

The mold 83 shown in FIGS. 12, 13, and 14 has the two halves 84 and 85 again made of R.T.V. molded silicone. The end 35 of the endotracheal tube is placed inside the mold 83 with the cuff 41 centered about the hollow cavity 87. With the mold 83 at room temperature, an inflating fluid enters the cuff 41 until it contacts the interior surface of the mold 83. This inflation causes the cuff 41 to expand to a diameter of 4.75 inches to reach the lateral edge 88 of the mold 83.

The end surfaces 88 and 89 of the mold 83 have a separation of 1.8 inches from each other. This is somewhat less than the 2.0 inches of the surfaces of 74 and 75 in the first mold of FIGS. 9 to 11.

After deflation, the cuff 41 retains a residual shape altered by its inflation in the mold 83. This residual shape appears in FIGS. 13 and 14.

As a result of the shaping in the mold 83, the cuff's edges 78 retain their original thickness of 0.008 inch. The portions 79 of the cuff 41 near the edge of the mold experience very little alteration from the mold in FIG. 12 and also retain their thickness of 0.007 inch. The interior portion 80 of the cuff 41, offset slightly from the cuff's center, achieves a thickness of 0.003 inch.

The very middle 81 of the cuff 41 has its thickness reduced to 0.002 inch, approximately one fourth of its original thickness. Thus, the cold-forming process reduces the thickness of the middle of the cuff 41 from 0.008 inch to 0.002 inch. The cold-forming process, in conjunction with the elastomeric, thermoplastic SEBS block copolymer, has produced a stretchable material having a thickness of 1/500 inch.

Moreover, the material has substantial elasticity and strength. Rather than weakening the elastomer, the overstretching involved in the cold forming appears to improve the strength and elasticity of the block copolymer.

Further, the use of molds in the cold-forming process avoids overstressing the thinner areas in the elastomer. As the cuff inflates, the thinner areas tend to expand preferentially. However, when they contact the mold's interior surface, they expand no further; the mold keeps these areas from continuing to expand primarily; from forming an aneurysm, and from breaking. With the thinner area no longer able to expand, the remaining portions of the material then expand and thin until they too contact the interior surface of the mold. In this fashion, the cold-forming process tends to equalize the thickness of the polymeric material.

The cold-forming process, by utilizing the molds such as in FIGS. 9 to 14, imparts a predetermined, accurate design to the elastomeric material. Moreover, since this material neither undergoes heating nor cooling, the process works quickly and achieves a high degree of efficiency.

The endotracheal tube employing a cuff formed from an elastomeric, thermoplastic hydrocarbon block copolymer with dispersed polysiloxane possesses several advantages over the devices previously semployed. In general, it results in less injury or discomfort to the patient.

When the cuff 41, as shown in FIG. 13, inflates within the patient's trachea, it has, due to the cold forming an increased effective area which actually contacts the patient's tissues. This area applies a gentle pressure to the tracheal wall and inflicts less damage than would a small area of the cuff 41, without the cold forming exerting a high pressure against the tracheal wall.

As shown in FIGS. 9 through 14 and as implied by its designation as an "elastomeric" material, the cuff formed of the polymer composition with dispersed polysiloxane actually increases in size when inflated. Consequently, prior to use, it may have a very small size and, thus, exhibit a low profile about the shaft of the endotracheal tube. Moreover, it has little or no folding over of material when totally deflated. This configuration of the deflated cuff adhering closely to the device's shaft with minimal or no projections provides a smooth surface to the patient's trachea during its insertion. As a consequence, it creates less patient discomfort or injury when introduced into the trachea.

Moreover, since the cuff begins without substantial folding over, it has none when inflated in the trachea. The endotracheal tube's cuff thus applies a smooth continuous surface against the tracheal wall as seen in FIG. 15. As shown there, the cuff 41 lies smoothly against the tracheal wall 94. It conforms closely to the hills 95 and valleys 96 resulting from the undulations in the tracheal wall. It also expands into depressions formed by irregularities in the tracheal wall. FIG. 16, by way of comparison, shows an endotracheal tube generally at 97 having a cuff 98 formed from polyvinylchloride. The PVC, being nonelastomeric, lies in folds about the tube's shaft even when deflated. Thus, when inflated sufficiently to contact the tracheal wall 94, the cuff 98 still has the folds or creases which run along its entire length. This permits the aspiration of fluids from the patient's mouth, such as saliva, into the patient's lungs. Sufficient fluid passing into the lungs in this fashion can induce pneumonia. The problem becomes especially exacerbated in tracheas having severe deformations and irregularities since the PVC simply cannot follow the shape of the trachea 96. Additionally, the folds 99 leave grooves and sores in the patient's trachea.

Moreover, the stiff polyvinylchloride of the cuff 98 does not conform to the trachea's hills 95 and valleys 96. Consequently, spaces 100 may remain between the tracheal wall 94 and the cuff 99 in the regions of the valleys 96 formed in the tracheal wall. Consequently, the polyvinylchloride exerts its pressure against the small hill areas of the tracheal wall 94. These elevated areas, under increased pressure, readily become sore and traumatized.

As discussed with regards to FIGS. 9 and 12, the cuff 41 formed of the present thermoplastic elastomer with dispersed polysiloxane can expand to 12 times its original size without bursting. It can easily inflate to 8 to 10 times its original diameter without adverse effects. This permits it to expand to the size required when used in an abnormally large trachea. Inflating the cuff until it contacts the tracheal wall becomes a safe procedure and provides assurance of a complete sealing of the trachea without bursting or substantial injury to the patient.

Furthermore, the high elasticity of the material results in only minimal increases in the internal pressure of the cuff as its volume increases. Thus, when the cuff reaches a sufficient size to contact the tracheal wall, it still exerts only minimal pressure against the tracheal wall. Consequently, fewer sizes of endotracheal tubes will suffice for the whole range of patients that a hospital encounters. Thus, the hospital can stock fewer sizes and reduce its inventory.

Furthermore, the elasticity of the material results in the exertion of only a low pressure against the tracheal wall when inflated to a sufficient volume to seal the trachea. This low pressure avoids the damage caused by conventional cuffs which exert a large lateral wall pressure.

Furthermore, the present material has a smooth, soft surface when inflated. This property, too, results in less irritation and less mucosal damage to the patient's tracheal wall.

The low pressure required to seal the cuff against the tracheal wall and the inherent softness of the present material allow it to facilely flex. This property becomes important in light of the fact that respiratory equipment often causes the endotracheal tube to pulsate slightly in and out of the patient's trachea. The soft cuff 41 absorbs this motion. As a result, the cuff 41 does not scrape against the tracheal wall. The PVC cuffs, by comparison, lack this softness and elasticity. As the respirator pulsates, the PVC cuffs actually scrape against the tracheal wall. Having a rough surface, they can and do injure the patient's trachea.

The present composition may also be used in the manufacture of balloon type catheters known in the art as Foley catheters. The composition can be used to form the entire catheter or only the balloon (or cuff) portion of the catheter.

The following examples utilize the polystyrene-ethylene-butylene-polystyrene (SEBS) polymer with a mineral oil lubricant sold as Kraton G 2705 by the Shell Chemical Company. The polymer pellets slowly receive the silicone oil which is used as the polysiloxane and the mixture tumbled together until the pellets achieve a uniform oil coating. Any additional ingredients, such as $BaSO_4$ or polypropylene, are sifted into the mixture at this point. The final mixture with all the ingredients then enter the hopper of the extruder which conveys it to its feed section.

In the following examples, the amounts of the ingredients are expressed as by weight percent. Furthermore, for the tensile strengths, standard die-punched dumbell specimens are tested at room temperature on an Instron tensile tester at 20 inches per minute.

EXAMPLES 1 to 7

A mixture of Kraton G 2705 SEBS resin pellets and 2 to 5 percent of a silicone oil is fed to a Brabender extruder. The particular oil used has a kinematic viscosity of 350 centistokes at room temperature and has undergone devolatilization prior to its use. The Dow Corning Company of Mich. provides this oil under the designation 360 Medical Grade.

To prepare an elastomer having 2 percent polysiloxane, 3 lbs. of the SEBS pellets are mixed with 27.21 gm. of the silicone oil. The extruded material ranges in thickness from 0.016 to 0.018 inch and displays a 100 percent elasticity modulus of 280 p.s.i.

The elongation and tensile strength of this 2 percent product appear in Table 1 along with the elastomers having 3, 4, and 5 percent silicone oil. In these latter examples, 40.82 gm., 54.43 gm., and 68.04 gm. of silicone oil, respectively, are added to the 3 lbs. of elastomer pellets.

Examples 2, 4, and 7 are performed at a different time than the others appearing in Table 1. The difference in these results for these materials may indicate a different pressure within the extruder. The material in these examples has a 100 percent elasticity modulus of 300 p.s.i.

TABLE 1

| Example | % Si Oil | % Elongation | Tensile p.s.i. |
|---------|----------|--------------|----------------|
| 1 | 2 | 800 | 2090 |
| 2 | 2 | 710 | 2300 |
| 3 | 3 | 650 | 1930 |
| 4 | 3 | 700 | 1960 |
| 5 | 4 | 560 | 1800 |
| 6 | 5 | 590 | 1690 |
| 7 | 5 | 710 | 1680 |

In heat seal tear tests performed on ½ inch guage material at 2 inches per minute, the composition of Example 2 with 2 percent silicone oil tested at 4.1 lbs./inch with 130 p.s.i. The material of Example 4 with 3 percent polysiloxane tested at 2.9 lbs./inch and 70 p.s.i.

EXAMPLES 8 and 9

In these examples, the SEBS pellets, in addition to the silicone oil, are mixed with 5 percent polypropylene with a melt flow of 12 according to ASTM Standard D-1238-70 and sold by Shell under the designation 5820. For the first of these runs, a mixture comprising 3 lbs. of the SEBS pellets, 40.82 gm. of the silicone oil described above, and 58.04 gm. of the polypropylene is fed to the same Brabender extruder. The extruded material ranges in thickness from 0.015 to 0.017 inch and displays a 100 percent elasticity modulus of 300 p.s.i.

Increasing the amount of silicone oil from 3 to 5 percent (54.43 gm.) provides a material having an increased elongation and the same tensile strength. Table 2 provides the results.

TABLE 2

| | 5% Polypropylene | | |
|---------|----------|--------------|----------------|
| Example | % Si Oil | % Elongation | Tensile p.s.i. |
| 8 | 3 | 620 | 2090 |
| 9 | 4 | 690 | 2090 |

EXAMPLES 10 to 12

In these examples, mixtures are prepared having 3 lbs. of the SEBS resin pellets and 204.12 gm. (15%) $BaSO_4$. The amount of silicone oil in these mixtures is varied from 3 percent (40.82 gm.), 4 percent (54.82 gm.) to 5 percent (58.04 gm.). The sheets produced by extruding these mixtures range in thickness from 0.014 to 0.16 inch and have a 100 percent elasticity modulus of 310 p.s.i. The elongation and tensile strength of these products appear in Table 3.

TABLE 3

| | 15% $BaSO_4$ | | |
|---------|----------|--------------|----------------|
| Example | % Si Oil | % Elongation | Tensile p.s.i. |
| 10 | 3 | 580 | 1530 |
| 11 | 4 | 650 | 1660 |
| 12 | 5 | 640 | 1490 |

EXAMPLES 13 to 15

The HPM extruder described above with a 2½ inch screw as shown in FIG. 5 is used to produce material having the most desirable properties. The screw has a 4:1 compression ratio and is rotated at 10 r.p.m. The three zones of the extruder operate at 185° C., 193° C., and 199° C., with the die at 204.5° C.

The extruder is fed a mixture having 2 percent (45.36 gm.) of the same silicone oil used previously with 5 lbs. of the Shell Kraton G 2705 pellets. The tubular product is extruded, in separate runs, to different wall thicknesses. The material has a 100 percent elasticity modulus of 250 p.s.i.

To produce a 0.010 inch tubular wall thickness, an 0.478 inch diameter die and a 0.456 inch pin are used in the extruder. The material is drawn down slightly after the extrusion. The percent elongation and tensile strength appear in Table 4 along with tubing having a wall thickness of 0.004 to 0.005 inch and, 0.0025 to 0.004 inch. As shown in Table 4, decreasing the wall thickness reduces the elongation and tensile strength of the tubing.

TABLE 4

2% Si Oil

| Example | Thickness-inch | % Elongation | Tensile p.s.i. |
|---------|----------------|--------------|----------------|
| 13 | .010 | 920 | 2320 |
| 14 | .004–.005 | 810 | 1640 |
| 15 | .0025–.004 | 610 | 1120 |

The above examples suggest that the polymer formed from the Shell Kraton G 2705 SEBS elastomer with about 2 to 4 percent silicone oil has the most desirable combination of high strength, low modulus, and maximum elongation. The addition of 5 percent polypropylene does not change the tensile strength of the produced material.

Adding 15 percent BaSO4 decreases the tensile strength of the resulting elastomer. The elongation, however, is increased. The BaSO4, in the compositions having from 3 to 4 percent silicone oil, also provides the resulting elastomer with a slight increase in rigidity.

EXAMPLE 16

A mixture having the following composition is prepared:

| Component | wt. gm. | wt. % |
|-----------|---------|-------|
| Kraton G-1651 (product of Shell Co.) | 90.3 | 30.08 |
| Kraton G-1650 (product of Shell Co.) | 38.7 | 12.89 |
| Polypropylene #5820 (product of Shell Co.) | 15.0 | 4.99 |
| Polypropylene #467 DP (product of Eastman Chem. Co.) | 9.0 | 2.99 |
| Antioxidant (Irganox #1010, product of Ciba-Geigy Corp.) | 0.15 | 0.05 |
| Silicone Oil #360 (product of Dow Corning)[1] | 12.0 | 4.00 |
| Mineral Oil (product of Witco Chemical Co.)[2] | 135.0 | 45.00 |
| | 300.15 | 100.00 |

[1]Kinematic viscosity = 12500 centistokes
[2]Viscosity = 350 centipoise

In the above mixture, the weight ratio of Kraton G-1651 to Kraton G-1650 is 70:30. The mixture is dry blended and then melt blended in a Banbury mixer at a full steam pressure of 110 p.s.i. for 3 to 5 minutes. The melt is then sheeted on a rubber mill at full steam pressure (110 p.s.i.) for 1 to 2 minutes. The milled sheets are either compression molded or extruded from cut strips. Test samples comprising 3 inches × ¼ inch × 0.07 inch razor cut strips are prepared and tested, with the following physical properties being obtained:
Shore A hardness: 46
% Elongation: 750
Tensile strength, p.s.i.: 810

EXAMPLE 17

Example 16 is repeated using a similar formula except that 96.9 gm of Kraton G-1651, 17.1 gm of Kraton G-1650 and 150 gm of mineral oil are used, the amounts for the other components being unchanged. In this mixture, the weight ratio of Kraton G-1651 to Kraton G-1650 is 85:15. This mixture yields a composition having the following properties:
Shore A hardness: 44
% Elongation: 880
Tensile strength, p.s.i.: 1000

EXAMPLE 18

Example 16 is repeated using a similar composition except that 57 gm of Kraton G-1651, 57 gm of Kraton G-1650 and 30 gm of polypropylene #5820 are used, the amounts of the other components remaining unchanged. In this mixture, the weight ratio of Kraton G-1651 to Kraton G-1650 is 50:50. This mixture yields a composition having the following properties:
Shore A hardness: 56
% Elongation: 605
Tensile strength, p.s.i.: 530

The results in Examples 16–18 show that blends of block copolymers also produce compositions having excellent properties.

What is claimed is:

1. A composition of matter comprising a substantially uniform mixture of (A) an elastomeric thermoplastic hydrocarbon block copolymer constituting greater than about 30% of the total weight of said composition and (B) a polysiloxane, said polysiloxane having a viscosity within the range of about 20 to 1,000,000 centistokes at room temperature and constituting about 0.1 to 12 percent of the total weight of said composition, said composition having improved surface properties and processability as a result of the incorporation of said polysiloxane.

2. The composition of claim 1 wherein said block copolymer has a total molecular weight in the range of about 50,000 to 600,000.

3. The composition of claim 2 wherein said polysiloxane is an essentially linear polysiloxane.

4. The composition of claim 3 further including a mineral oil dispersed substantially uniformly throughout said composition, said mineral oil comprising about 5 to 60 percent of the total weight of said composition.

5. The composition of claim 4 wherein said block copolymer is a styrene-ethylene-butylene-styrene block copolymer.

6. The composition of claim 5 wherein the styrene blocks of said copolymer have a molecular weight of about 5,000 to 40,000 and the ethylene-butylene block of said copolymer has a molecular weight of about 20,000 to 500,000.

7. The composition of claim 6 wherein the sytrene blocks comprise about 20 to 50 percent of the total weight of said copolymer and the ethylene-butylene block comprises about 50 to 80 percent of the weight of said copolymer.

8. The composition of claim 7 wherein the styrene blocks of said copolymer have a molecular weight in the range of about 8,000 to 20,000 and the ethylene-butylene block of said copolymer has a molecular weight of about 20,000 to 200,000.

9. The composition of claim 8 wherein said polysiloxane has the repeating structure:

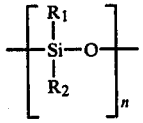

wherein $R_1$, $R_2 =$ H, $CH_3$, or

and n is a positive integer having a value between 10 and 20,000.

10. The composition of claim 9 wherein said polysiloxane has a kinematic viscosity of about 200 to 13,000 centistokes.

11. The composition of claim 10 wherein the polysiloxane of said composition has been devolatilized.

12. The composition of claim 11 wherein $R_1$ and $R_2$ are both $CH_3$.

13. The composition of claim 12 wherein said polysiloxane constitutes about 1 to 12 percent of the total weight of said composition.

14. The composition of claim 13 further including polypropylene distributed substantially uniformly throughout said composition, said polypropylene constituting less than about 45 percent of the total weight of said composition.

15. The composition of claim 14 wherein said polypropylene constitutes about 2 to 20 percent of the total weight of said composition.

16. The composition of claim 5 wherein the composition comprises at least one additional elastomer thermoplastic hydrocarbon block copolymer having different amounts of styrene and ethylene-butylene blocks from that of copolymer (A).

17. A composition of matter comprising a substantially uniform mixture of:
(A) at least one elastomeric, thermoplastic hydrocarbon block copolymer, said copolymer having a total molecular weight of about 50,000 to 600,000, the total amount of block copolymer constituting greater than about 30% of the total weight of said composition;
(B) an essentially linear polysiloxane having a kinematic viscosity of about 20 to 1,000,000 centistokes at room temperature, and constituting about 0.1 to 12 percent of the total weight of said composition; and
(C) a mineral oil constituting less than about 60 percent of the total weight of said composition, said composition having improved surface properties and processability as a result of the incorporation of said polysiloxane.

18. The composition of claim 17 further including polypropylene which constitutes less than about 45 percent of the total weight of said composition.

19. The composition of claim 18 wherein said block copolymer has an A—B—A configuration wherein A is a monovinylarene polymer block and B is a hydrogenated or nonhydrogenated conjugated diene polymer block.

20. The composition of claim 19 wherein:
(A) said block copolymer is a styrene-ethylene-butylene-styrene block copolymer;
(B) said polysiloxane comprises about 0.1 to 12 percent of the total weight of said composition;
(C) said mineral oil comprises about 25 to 50 percent of the total weight of said composition; and
(D) said polypropylene comprises about 5 to 10 percent of the total weight of said composition.

21. The composition of claim 20 wherein the styrene blocks of said copolymer have a molecular weight of about 8,000 to 20,000 and comprises about 20 to 50 percent of the total weight of said copolymer and the ethylene-butylene block has a molecular weight of about 20,000 to 500,000 and comprises about 50 to 80 percent of the total weight of said copolymer.

22. A composition of matter comprising a substantially uniform mixture of:
(A) at least one elastomeric, thermoplastic A—B—A block copolymer, where A is a monovinylarene polymer block and B is a hydrogenated or nonhydrogenated conjugated diene polymer block, the total amount of block copolymer constituting greater than about 30% of the total weight of said composition;
(B) an essentially linear polysiloxane having a kinematic viscosity of about 20 to 1,000,000 centistokes at room temperature and constituting about 0.1 to 12 percent of the total weight of said composition; and
(C) a mineral oil constituting less than about 60 percent of the total weight of said composition, said composition having improved surface properties and processability as a result of the incorporation of said polysiloxane.

23. The composition of claim 22 further including polypropylene which constitutes less than about 45 percent of the total weight of said composition.

24. The composition of claim 23 wherein:
(A) said block copolymer is a styrene-ethylene-butylene-styrene block copolymers;
(B) said polysiloxane comprises about 0.1 to 12 percent of the total weight of said composition;
(C) said mineral oil comprises about 25 to 50 percent of the total weight of said composition; and
(D) said polypropylene comprises about 5 to 10 percent of the total weight of said composition.

25. The composition of claim 24 wherein the styrene blocks of said copolymer have a molecular weight of about 5,000 to 40,000 and comprises about 20 to 50 percent of the total weight of said copolymer and the ethylene-butylene block has a molecular weight of about 20,000 to 500,000 and comprises about 50 to 80 percent of the total weight of said copolymer.

* * * * *